US00PP13444P3

(12) United States Plant Patent
Cain

(10) Patent No.: US PP13,444 P3
(45) Date of Patent: Dec. 31, 2002

(54) GRAPEVINE CV. 'SUGRATWENTYONE'

(75) Inventor: David W. Cain, Bakersfield, CA (US)

(73) Assignee: Sun World International, Inc., Bakersfield, CA (US)

( * ) Notice: Subject to any disclaimer, the term of this patent is extended or adjusted under 35 U.S.C. 154(b) by 1 day.

(21) Appl. No.: 09/771,294

(22) Filed: Jan. 25, 2001

(65) Prior Publication Data

US 2002/0100086 P1 Jul. 25, 2002

(51) Int. Cl.[7] ..... A01H 5/00
(52) U.S. Cl. ..... Plt./205
(58) Field of Search ..... Plt./205

(56) References Cited

U.S. PATENT DOCUMENTS

PP4,787 P 11/1981 Olmo et al. ..... Plt./47

*Primary Examiner*—Bruce R. Campell
*Assistant Examiner*—Michelle Kizilkaya
(74) *Attorney, Agent, or Firm*—Knobbe, Martens, Olson & Bear

(57) ABSTRACT

A new and distinct grapevine variety characterized by naturally large, red, seedless berries that are crisp, round and uniform. Berries of the new 'Sugratwentyone' variety are thin-skinned and are strongly attached to large, slightly compact clusters.

1 Drawing Sheet

BACKGROUND AND SUMMARY OF THE INVENTION

This invention relates to the discovery and asexual propagation of a new variety of grapevine, *Vitis vinifera* cv. 'Sugratwentyone'. The new variety was first hybridized by David W. Cain in Wasco, Kern County, Calif., the variety being originated by controlled bybridization and subsequent ovule culture of normally abortive seeds. The new 'Sugratwentyone' variety is characterized by producing large clusters of red, naturally large seedless berries that are uniform, crisp and round.

The seed parent is 'Sun World Breeding Selection 90089-165-268' (nonpatented). The pollen parent is 'Sun World International Breeding Selection 90227-127-008' (nonpatented). The parent varieties were first crossed in May, 1993, with the date of first flowering being May, 1995. The new 'Sugratwentyone' variety was first asexually propagated by David W. Cain in December, 1995, near Wasco, Kern County, Calif., using hardwood cuttings.

The new grapevine variety cv. 'Sugratwentyone' differs from its seed parent by producing larger, more nearly round light red berries (as compared to the smaller, reddish-black berries of the seed parent) that ripen approximately one month later. 'Sugratwentyone' differs from its pollen parent by producing berries that are rounder and light red in color, in comparison to the oval, black berries of the pollen parent.

The new variety cv. 'Sugratwentyone' can be distinguished from commonly grown grape varieties such as the 'Redglobe' (U.S. Plant Pat. No. 4,787) and the 'Flame Seedless' (nonpatented) by possessing large clusters of red seedless berries that are crisp and uniform. The berries of the new 'Sugratwentyone' variety color with some difficulty in hot conditions, and are prone to bunch rot due to a combination of thin skin and a slightly compact cluster structure. Moreover, the berries of 'Sugratwentyone' are naturally very large, being among the largest of known seedless grapes. Manipulation by either gibberellic acid or girdling produces berries that are even larger. The berries are strongly attached to the cluster, mainly due to increased lignification of the peduncle, rachis, pedicel, and torus.

'Sugratwentyone' most nearly resembles the 'Redglobe' variety, but is distinguished from 'Redglobe' by forming berries that are slightly smaller and contain small, vestigial seed remnants as compared to the 'Redglobe' variety. The new variety cv. 'Sugratwentyone' remotely resembles the 'Flame Seedless' variety, but produces berries that are naturally much larger, ripening about six weeks after the 'Flame Seedless' variety.

The new 'Sugratwentyone' variety has been shown to maintain its distinguishing characteristics through successive asexual propagations by, for example, cuttings.

BRIEF DESCRIPTION OF THE FIGURE

The accompanying drawing in FIG. 1 illustrates in full color a typical cluster of berries, a young shoot, and a mature leaf blade of the new grapevine.

DETAILED BOTANICAL DESCRIPTION OF THE INVENTION

Figure 1:
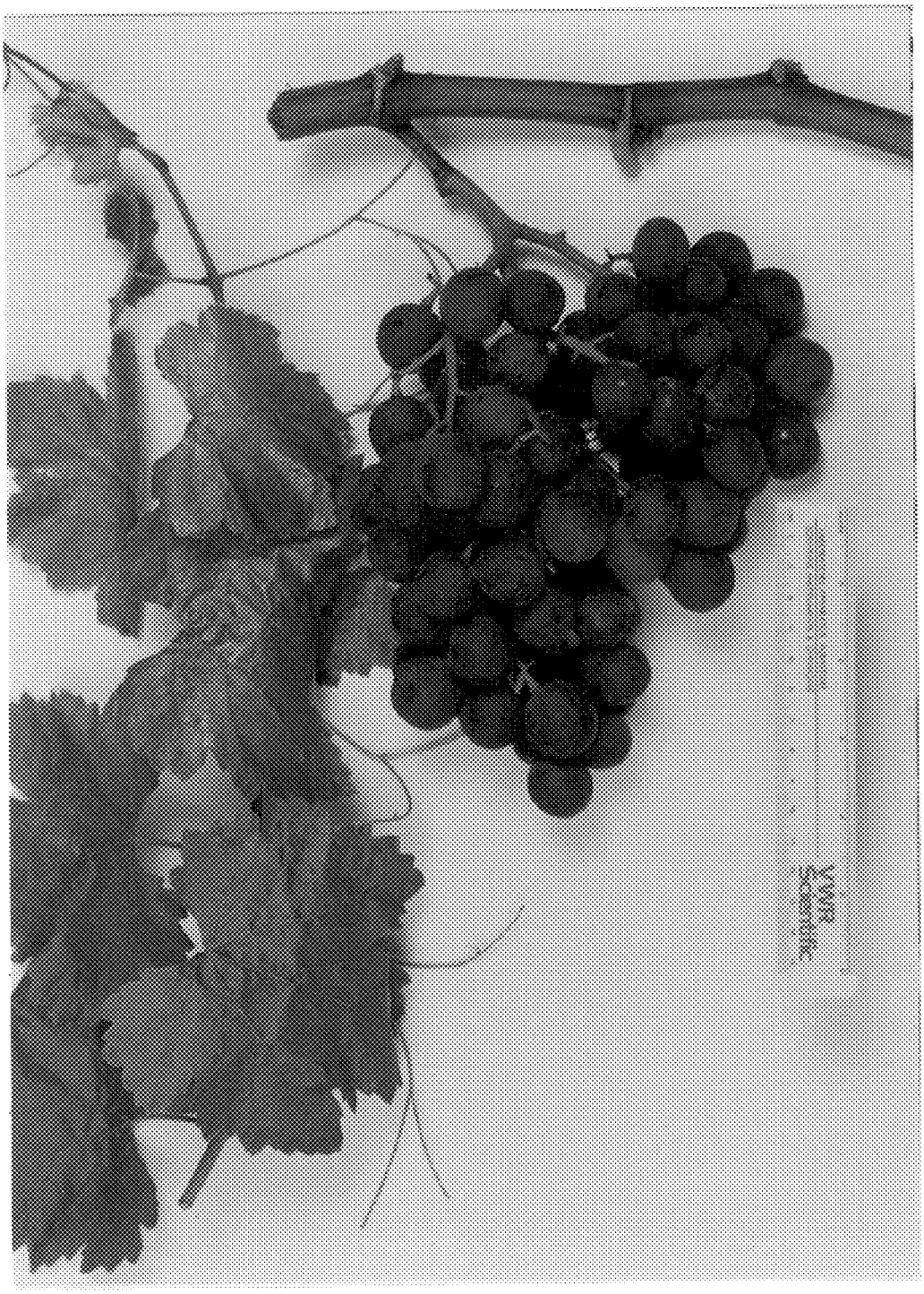

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England.

Many of the description values in this specification are based on and conform to those set forth by the International Board for Plant Genetic Resources Institute Grape Descriptors (Vitis spp.) of 1983 and/or 1997 which was developed in collaboration with the Office International de la Vigne et du Vin (OIV) and the International Union for the Protection of New Varieties of Plants (UPOV).

The descriptive matter which follows pertains to 'Sugratwentyone' plants grown in the vicinity of Wasco, Kern County, Calif., during 2000, and is believed to apply to plants of the variety grown under similar conditions of soil and climate elsewhere:

VINE

General:
*Size*.—Small.
*Vigor*.—Weak.
*Density of foilage*.—Medium to open.
*Productivity*.—Productive.
*Root stock*.—Own root.

Trunk:
*Shape*.—Medium.
*Straps*.—Long.
*Surface texture*.—Shaggy.
*Inner bark color*.—About 177B.

SHOOTS

Young shoot:
*Form of tip*.—Wide open.
*Distribution of anthocyanin coloration of tip*.—Absent.
*Intensity of anthocyanin coloration of tip*.—Absent.
*Density of prostrate hairs on tip*.—Very sparse.
*Density of erect hairs on tip*.—Absent.

Flowering shoot:
*Vigor during flowering*.—Medium.
*Attitude during flowering on shoots which are not tied*.—Horizontal.
*Color of dorsal side of internodes*.—About green 144A.
*Color of ventral side of internodes*.—About green 144A.
*Color of dorsal side of nodes*.—About green 144A.
*Color of ventral side of nodes*.—About green 144A.
*Density of erect hairs on nodes*.—None.
*Erect hairs on internode*.—Absent.
*Density of prostrate hairs on nodes*.—None.
*Density of prostrate hairs on internodes*.—Absent.
*Anthocyanin coloration of buds*.—Absent.

Tendrils:
*Distribution on the shoot at full flowering*.—Discontinuous.
*Thickness*.—Medium.
*Color*.—About 144B.
*Form*.—Trifurcated.
*Number of consecutive tendrils*.—Up to two.
*Length of tendril*.—Short to medium, about 18.2 cm.

LEAVES

Young leaves:
*Color of upper surface of first 4 distal unfolded leaves*.—Copper yellow.
*Average intensity of anthocyanin coloration of six distal leaves prior to flowering*.—Very weak to weak.
*Density of prostrate hairs between veins at lower surface of 4th distal unfolded leaf*.—Absent.
*Density of erect hairs between veins at lower surface of 4th distal unfolded leaf*.—Absent.
*Density of prostrate hairs on veins at lower surface of 4th distal unfolded leaf*.—Very sparse.
*Density of erect hairs on veins at lower surface of 4th distal unfolded leaf*.—Absent.

Mature leaves:
*Average length*.—About 15.4 cm.
*Average width*.—About 16.8 cm.
*Size of blade*.—Medium.
*Shape of blade*.—Pentagonal.
*Number of lobes*.—3 to 5.
*Anthocyanin coloration of main veins on the upper side of the blade*.—Absent.
*Mature leaf profile*.—Undulate.
*Blistering surface of blade upper surface*.—Medium.
*Leaf blade tip*.—In the plane of the leaf.
*Undulation of margin*.—Medium.
*Apex*.—Cuspidate.
*Thickness*.—Medium.
*Undulation of blade between main and lateral veins*.—Only near petiole.
*Shape of teeth*.—Both sides convex.
*Length of teeth*.—Medium.
*Ratio length/width of teeth*.—Medium.
*General shape of petiole sinus*.—Slightly open.
*Tooth at petiole sinus*.—Present.
*Petiole sinus limited by veins*.—Absent.
*Shape of upper lateral sinus*.—Closed to lobes slightly overlapping.
*Depth of upper lateral sinus*.—Medium.
*Density of prostrate hairs between veins on lower surface of blade*.—Absent.
*Density of erect hairs between veins on lower surface of blade*.—Absent.
*Density of prostrate hairs on main veins on lower surface of blade*.—None or very sparse.
*Density of erect hairs on main veins on lower surface of blade*.—Sparse.
*Density of prostrate hairs on main veins on upper surface of blade*.—Absent.
*Autumn coloration of leaves*.—About yellow 11B (color development occurs late, and leaves are typically killed by frost before extensive color change).

Upper surface:
*Color*.—About 137A.
*Surface texture*.—Rugose.
*Surface appearance*.—Semi-glossy.
*Goffering of blade*.—Absent.

Lower surface:
*Color*.—About 137C.
*Anthocyanin coloration of main veins on lower leaf surface*.—Absent.
*Glossiness*.—Weak.
*Pubescence*.—Absent.
*Surface texture*.—Rugose.

Petiole:
*Length of petiole*.—Long, about 14.4 cm.
*Length of petiole compared to middle vein*.—Slightly shorter.
*Density of prostrate hairs on petiole*.—None.
*Density of erect hairs on petiole*.—None.
*Shape of base of petiole sinus*.—V-shaped.

Woody shoot:
*Shape*.—Medium.
*Internode length*.—Medium, about 91.6 mm.
*Width at node*.—About 14.6 mm.
*Cross section*.—Circular.
*Surface*.—Striate.
*Main color*.—About yellowish brown 166C.
*Lenticels*.—Absent.
*Density of erect hairs on nodes*.—None.
*Density of erect hairs on internodes*.—None.
*Growth of axillary shoots*.—Very weak, about 14.7 cm.

Buds:

*Shape*.—Pointed.

*Size*.—Medium, about 0.05 cm length by 0.54 cm width.

*Position*.—Slightly held out.

*Cane bud fruitfulness*.—Basal most fruitful, seldom dead.

*Time of bud burst*.—Late.

FLOWERS

General:

*Flowers sex*.—Hermaphrodite.

*Length of first inflorescence*.—Medium, about 16.4 cm.

*Position of first flowering node*.—$3^{rd}$.

*Number of inflorescences per shoot*.—1.1 to 2.

*Date of full bloom*.—May 4, 2000.

*Time of bloom*.—Late, as compared with similar varieties in the growing area of Wasco, Kern County, Calif.

*Size* (*diameter of fully open flower*).—Large.

FRUIT

General:

*Ripening period*.—Medium to late, about 25 days after the unpatented 'Thompson Seedless' variety.

*Use*.—Fresh market.

*Keeping quality*.—Medium.

*Resistance*.—Insects: Medium. Diseases: Medium.

*Shipping quality*.—Good.

*Date of first harvest*.—Aug. 20, 2000.

*Solids-sugar*.—Low (~15%) to medium (~18%).

*Refractometer test*.—16.7° brix.

*Acid*.—Low, about 42 g/L tartaric acid.

*Juice pH*.—4.24 (on Oct. 13, 2000).

Cluster:

*Bunch size* (*peduncle excluded*).—Large.

*Bunch length* (*peduncle excluded*).—Intermediate, about 18.5 cm.

*Bunch width*.—About 13.6 cm.

*Bunch weight*.—Medium to high, averaging about 548.6 g.

*Bunch density*.—Medium.

*Number of berries*.—About 80.2.

*Form*.—Conical.

Peduncle:

*Length of peduncle*.—Short to medium, about 4.5 cm.

*Lignification of peduncle*.—Strong.

*Color*.—About 144B.

Berry:

*Size*.—Very large.

*Uniformity of size*.—Uniform.

*Berry weight*.—Very high, about 8.7 g, or up to 13.9 g with girdling and gibberellic acid application.

*Shape*.—Round.

*Presence of seeds*.—Rudimentary, about 2.16 mg/seed.

*Cross section*.—Circular.

*Dimensions*.—About 25.6 mm longitudinal axis, 25.2 mm horizontal axis.

*Skin color* (*without bloom*).—Red-Grey, about 184B Greyed Purple group.

*Coloration of flesh*.—Clear.

*Juiciness of flesh*.—Slightly juicy.

*Berry firmness*.—Firm.

*Particular flavor*.—None.

*Bloom* (*cuticular wax*).—Medium.

*Pedicel length*.—Intermediate, about 9.3 mm.

*Berry separation from pedicel*.—Very difficult.

*Visibility of hilum*.—Slightly clear.

*Torus*.—Large.

Skin:

*Thickness*.—Thin.

*Texture*.—Tender.

*Reticulation*.—Absent.

*Roughness*.—Absent.

*Tenacity*.—Tenacious to flesh.

*Tendency to crack*.—None.

What is claimed is:

1. A new and distinct variety of grapevine cv. 'Sugratwentyone' as herein illustrated and described.

* * * * *